United States Patent
Rodgers et al.

(10) Patent No.: US 6,218,386 B1
(45) Date of Patent: *Apr. 17, 2001

(54) A1-(3-AMINOINDAZOL-5-YL)-3 BUTYL-CYCLIC UREA USEFUL AS A HIV PROTEASE INHIBITOR

(75) Inventors: James David Rodgers, Landenberg; Patrick Yuk-Sun Lam, Chadds Ford, both of PA (US)

(73) Assignee: Dupont Pharmaceuticals, Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/966,426

(22) Filed: Nov. 7, 1997

Related U.S. Application Data

(60) Provisional application No. 60/029,746, filed on Nov. 8, 1996.
(51) Int. Cl.⁷ .................................................. A61K 31/551
(52) U.S. Cl. ........................ 514/218; 514/221; 540/492; 540/503
(58) Field of Search .................................. 540/492, 503; 514/218, 221

(56) References Cited

U.S. PATENT DOCUMENTS 5,521,161  5/1996  Malley et al. .
5,532,357  7/1996  Rodgers et al. .
5,610,294  3/1997  Lam et al. .

FOREIGN PATENT DOCUMENTS 9629329  9/1996  (WO) .

OTHER PUBLICATIONS

Vila et al, *Lancet* 1997, 350 635–636, "Absence of viral rebound after treatment of HIV–infected patients with didanosine and hydroxycarbamide".

*Primary Examiner*—Richard L. Raymond
(74) *Attorney, Agent, or Firm*—David H. Vance

(57) ABSTRACT

The present invention relates to compounds of formula I:

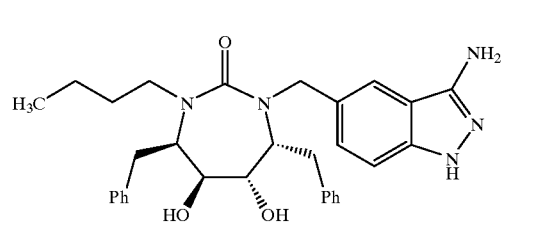

or pharmaceutically acceptable salt forms or prodrugs thereof, which are useful as inhibitors of HIV protease, and to pharmaceutical compositions and diagnostic kits comprising the same, and methods of using the same for treating viral infection or as an assay standard or reagent.

16 Claims, No Drawings

A1-(3-AMINOINDAZOL-5-YL)-3 BUTYL-CYCLIC UREA USEFUL AS A HIV PROTEASE INHIBITOR

This application claims the benefit of U.S. Provisional Application No. 60/029,746, filed Nov. 8, 1996.

FIELD OF THE INVENTION

This invention relates generally to a 1-(3-aminoindazol-5-yl)-3-butyl-cyclic urea which is useful as inhibitors of HIV protease, pharmaceutical compositions and diagnostic kits comprising the same, and methods of using the same for treating viral infection or as assay standards or reagents.

BACKGROUND OF THE INVENTION

Two distinct retroviruses, human immunodeficiency virus (HIV) type-1 (HIV-1) or type-2 (HIV-2), have been etiologically linked to the immunosuppressive disease, acquired immunodeficiency syndrome (AIDS). HIV seropositive individuals are initially asymptomatic but typically develop AIDS related complex (ARC) followed by AIDS. Affected individuals exhibit severe immunosuppression which predisposes them to debilitating and ultimately fatal opportunistic infections.

The disease AIDS is the end result of an HIV-1 or HIV-2 virus following its own complex life cycle. The virion life cycle begins with the virion attaching itself to the host human T-4 lymphocyte immune cell through the bonding of a glycoprotein on the surface of the virion's protective coat with the CD4 glycoprotein on the lymphocyte cell. Once attached the virion sheds its glycoprotein coat, penetrates into the membrane of the host cell, and uncoats its RNA. The virion enzyme, reverse transcriptase, directs the process of transcribing the RNA into single-stranded DNA. The viral RNA is degraded and a second DNA strand is created. The now double-stranded DNA is integrated into the human cell's genes and those genes are used for cell reproduction.

At this point, the human cell carries out its reproductive process by using its own RNA polymerase to transcribe the integrated DNA into viral RNA. The viral RNA is translated into the precursor gag-pol fusion polyprotein. The polyprotein is then cleaved by the HIV protease enzyme to yield the mature viral proteins. Thus, HIV protease in responsible for regulating a cascade of cleavage events that lead to the virus particle's maturing into a virus that is capable of full infectivity.

The typical human immune system response, killing the invading virion, is taxed because a large portion of the virion's life cycle is spent in a latent state within the immune cell. In addition, viral reverse transcriptase, the enzyme used in making a new virion particle, is not very specific, and causes transcription mistakes that result in continually changed glycoproteins on the surface of the viral protective coat. This lack of specificity decreases the immune system's effectiveness because antibodies specifically produced against one glycoprotein may be useless against another, hence reducing the number of antibodies available to fight the virus. The virus continues to reproduce while the immune response system continues to weaken. Eventually, the HIV largely holds free reign over the body's immune system, allowing opportunistic infections to set in and without the administration of antiviral agents, immunomodulators, or both, death may result.

There are at least three critical points in the virus's life cycle which have been identified as possible targets for antiviral drugs: (1) the initial attachment of the virion to the T-4 lymphocyte or macrophage site, (2) the transcription of viral RNA to viral DNA (reverse transcriptase, RT), and (3) the assemblage of the new virus particle during reproduction (e.g., HIV aspartic acid protease or HIV protease).

The genomes of retroviruses encode a protease that is responsible for the proteolytic processing of one or more polyprotein precursors such as the pol and gag gene products. See Wellink, Arch. Virol. 98 1 (1988). Retroviral proteases most commonly process the gag precursor into the core proteins, and also process the pol precursor into reverse transcriptase and retroviral protease.

The correct processing of the precursor polyproteins by the retroviral protease is necessary for the assembly of the infectious virions. It has been shown that in vitro mutagenesis that produces protease-defective virus leads to the production of immature core forms which lack infectivity. See Crawford et al., J. Virol. 53 899 (1985); Katoh et al., Virology 145 280 (1985). Therefore, retroviral protease inhibition provides an attractive target for antiviral therapy. See Mitsuya, Nature 325 775 (1987).

The ability to inhibit a viral protease provides a method for blocking viral replication and therefore a treatment for viral diseases, such as AIDS, that may have fewer side effects, be more efficacious, and be less prone to drug resistance when compared to current treatments. As a result, three HIV protease inhibitors, Roche's saquinavir, Abbott's ritonavir, and Merck's indinavir, are currently being marketed and a number of potential protease inhibitors are in clinical trials, e.g., Vertex's VX-478, Agouron's nelfinavir, Japan Energy's KNI-272, and Ciba-Geigy's CGP 61755.

As evidenced by the protease inhibitors presently marketed and in clinical trials, a wide variety of compounds have been studied as potential HIV protease inhibitors. One core, cyclic ureas, has received significant attention. For example, in PCT Application Number WO94/19329, Lam et al generically describe cyclic ureas of the formula:

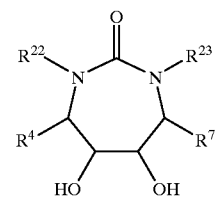

and methods of preparing these ureas. Though the present compounds fall within the description of Lam et al, they are not specifically disclosed therein.

Even with the current success of protease inhibitors, it has been found that HIV patients can become resistant to a single protease inhibitor. Thus, it is desirable to develop additional protease inhibitors to further combat HIV infection.

SUMMARY OF THE INVENTION

Accordingly, one object of the present invention is to provide novel protease inhibitors.

It is another object of the present invention to provide pharmaceutical compositions with protease inhibiting activity comprising a pharmaceutically acceptable carrier and a therapeutically effective amount of at least one of the compounds of the present invention or a pharmaceutically acceptable salt or prodrug form thereof.

It is another object of the present invention to provide a novel method for treating HIV infection which comprises administering to a host in need of such treatment a therapeutically effective amount of at least one of the compounds of the present invention or a pharmaceutically acceptable salt or prodrug form thereof.

It is another object of the present invention to provide a novel method for treating HIV infection which comprises administering to a host in need thereof a therapeutically effective combination of (a) one of the compounds of the present invention and (b) one or more compounds selected form the group consisting of HIV reverse transcriptase inhibitors and HIV protease inhibitors.

It is another object of the present invention to provide a method of inhibiting HIV present in a body fluid sample which comprises treating the body fluid sample with an effective amount of a compound of the present invention.

It is another object of the present invention to provide a kit or container containing at least one of the compounds of the present invention in an amount effective for use as a standard or reagent in a test or assay for determining the ability of a potential pharmaceutical to inhibit HIV protease, HIV growth, or both.

These and other objects, which will become apparent during the following detailed description, have been achieved by the inventors' discovery that compounds of formula I:

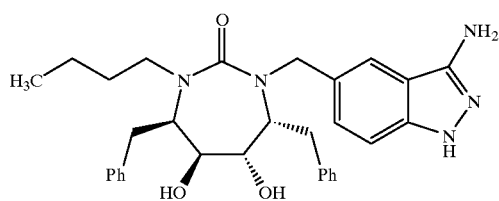

or pharmaceutically acceptable salts or prodrug forms thereof, are effective protease inhibitors.

DETAILED DESCRIPTION OF PREFERRED EMBODIMENTS

Thus, in a first embodiment, the present invention provides a novel compound of formula I:

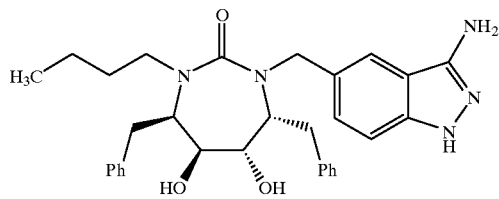

or a pharmaceutically acceptable salt or prodrug form thereof.

In a second embodiment, the present invention provides a novel pharmaceutical composition comprising a pharmaceutically acceptable carrier and a therapeutically effective amount of a compound of formula I or a pharmaceutically acceptable salt or prodrug form thereof.

In a third embodiment, the present invention provides a novel method for treating HIV infection which comprises administering to a host in need of such treatment a therapeutically effective amount of a compound of formula I or a pharmaceutically acceptable salt or prodrug form thereof.

In a fourth embodiment, the present invention provides a novel method of treating HIV infection which comprises administering, in combination, to a host in need thereof a therapeutically effective amount of:
  (a) a compound of formula I; and,
  (b) at least one compound selected from the group consisting of HIV reverse transcriptase inhibitors and HIV protease inhibitors.

In another preferred embodiment, the reverse transcriptase inhibitor is a nucleoside reverse transcriptase inhibitor.

In another more preferred embodiment, the nucleoside reverse transcriptase inhibitor is selected from AZT, 3TC, ddI, ddC, and d4T and the protease inhibitor is selected from saquinavir, ritonavir, indinavir, VX-478, nelfinavir, KNI-272, CGP-61755, and U-103017.

In an even more preferred embodiment, the nucleoside reverse transcriptase inhibitor is selected from AZT and 3TC and the protease inhibitor is selected from saquinavir, ritonavir, and indinavir.

In a still further preferred embodiment, the nucleoside reverse transcriptase inhibitor is AZT.

In another still further preferred embodiment, the protease inhibitor is indinavir.

In a fifth embodiment, the present invention provides a pharmaceutical kit useful for the treatment of HIV infection, which comprises a therapeutically effective amount of:
  (a) a compound of formula I; and,
  (b) at least one compound selected from the group consisting of HIV reverse transcriptase inhibitors and HIV protease inhibitors, in one or more sterile containers.

In a sixth embodiment, the present invention provides a novel method of inhibiting HIV present in a body fluid sample which comprises treating the body fluid sample with an effective amount of a compound of formula I.

In a seventh embodiment, the present invention to provides a novel a kit or container comprising a compound of formula I or II in an amount effective for use as a standard or reagent in a test or assay for determining the ability of a potential pharmaceutical to inhibit HIV protease, HIV growth, or both.

DEFINITIONS

As used herein, the following terms and expressions have the indicated meanings. It will be appreciated that the compounds of the present invention contain an asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

As used herein, "HIV reverse transcriptase inhibitor" is intended to refer to both nucleoside and non-nucleoside inhibitors of HIV reverse transcriptase (RT). Examples of nucleoside RT inhibitors include, but are not limited to, AZT, ddC, ddI, d4T, and 3TC. Examples of non-nucleoside RT inhibitors include, but are no limited to, viviradine (Pharmacia and Upjohn U90152S), TIBO derivatives, BI-RG-587, nevirapine, L-697,661, LY 73497, and Ro 18,893 (Roche).

As used herein, "HIV protease inhibitor" is intended to refer to compounds which inhibit HIV protease. Examples include, but are not limited, saquinavir (Roche, Ro31-8959), ritonavir (Abbott, ABT-538), indinavir (Merck, MK-639), VX-478 (Vertex/Glaxo Wellcome), nelfinavir (Agouron, AG-1343), KNI-272 (Japan Energy), CGP-61755 (Ciba-Geigy), and U-103017 (Pharmacia and Upjohn). Additional examples include the cyclic protease inhibitors disclosed in WO93/07128, WO 94/19329, WO 94/22840, and PCT Application Number US96/03426.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Prodrugs" are intended to include any covalently bonded carriers which release the active parent drug according to formula I or other formulas or compounds of the present invention in vivo when such prodrug is administered to a mammalian subject. Prodrugs of a compound of the present invention, for example formula (I), are prepared by modifying functional groups present in the compound in such a way that the modifications are cleaved, either in routine manipulation or in vivo, to the parent compound. Prodrugs include compounds of the present invention wherein the hydroxy or amino group is bonded to any group that, when the prodrug is administered to a mammalian subject, cleaves to form a free hydroxyl or free amino, respectively. Examples of prodrugs include, but are not limited to, acetate, formate, or benzoate derivatives of alcohol and amine functional groups in the compounds of formula I; phosphate esters, dimethylglycine esters, aminoalkylbenzyl esters, aminoalkyl esters and carboxyalkyl esters of alcohol functional groups in the compounds of formula I; and the like. Additional examples include compounds wherein the two hydroxy groups of formula I join to form an epoxide; $-OCH_2SCH_2O-$; $-OC(=O)O-$; $-OCH_2O-$; $-OC(=S)O-$; $-OC(=O)C(=O)O-$; $-OC(CH_3)_2O-$; $-OC((CH_2)_3NH_2)(CH_3)O-$; $-OC(OCH_3)(CH_2CH_2CH_3)O-$; or $-OS(=O)O-$.

"Stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., $=O$) group, then 2 hydrogens on the atom are replaced.

"Therapeutically effective amount" is intended to include an amount of a compound of the present invention or an amount of the combination of compounds claimed effective to inhibit HIV infection or treat the symptoms of HIV infection in a host. The combination of compounds is preferably a synergistic combination. Synergy, as described for example by Chou and Talalay, Adv. Enzyme Regul. 22:27–55 (1984), occurs when the effect (in this case, inhibition of HIV replication) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

Other features of the invention will become apparent in the course of the following descriptions of exemplary embodiments which are given for illustration of the invention and are not intended to be limiting thereof.

EXAMPLES

Abbreviations used in the Examples are defined as follows: "°C." for degrees Celsius, "d" for doublet, "dd" for doublet of doublets, "eq" for equivalent or equivalents, "g" for gram or grams, "mg" for milligram or milligrams, "mL" for milliliter or milliliters, "H" for hydrogen or hydrogens, "hr" for hour or hours, "m" for multiplet, "M" for molar, "min" for minute or minutes, "MHz" for megahertz, "MS" for mass spectroscopy, "nmr" or "NMR" for nuclear magnetic resonance spectroscopy, "t" for triplet, and "TLC" for thin layer chromatography.

Example 1

Preparation of (4R, 5S, 6S, 7R)-Hexahydro-1-[5-(3-aminoindazole)methyl]-3-butyl-5,6-dihydroxy-4,7-bis[phenylmethyl]-2H-1,3-diazapin-2-one (I).

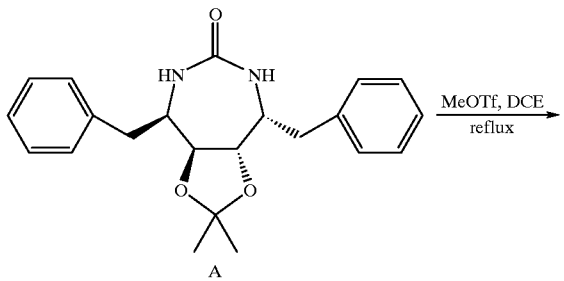

A

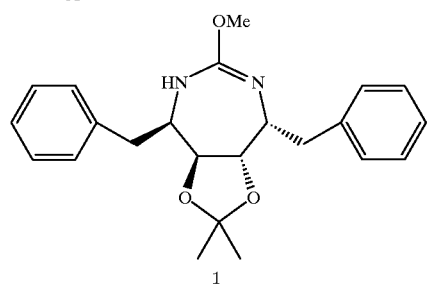

1

Compound A can be prepared by known methods. For example, preparation of compound A is shown in Scheme 1 of Rossano et al (*Tetr. Lett.* 1995, 36(28), 4967, 4968), the contents of which are hereby incorporated by reference. An additional method of preparation of compound A is shown in Example 6 of U.S. Pat. No. 5,530,124, the contents of which are hereby incorporated by reference.

PART A: To a suspension of compound 1 (10.0 g; 27.3 mmol) in 1,2-dichloroethane (100 mL) was added methyltriflate (3.4 mL, 30 mmol). After refluxing overnight, the reaction was washed with sat. NaHCO$_3$, sat. NaCl, dried (Na$_2$SO$_4$) and evaporated leaving 12.5 g of a yellow oil. Column chromatography (flash SiO$_2$; 25% EtOAc/hexane) gave 7.86 g of compound 2 as a pale yellow oil which crystallized on standing (75% yield). m.p.=97–100° C. MH$^+$=381.

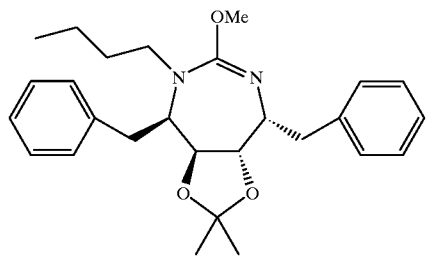

2

PART B: To a solution of 1 (10.0 g, 26.3 mmol) in anhydrous DMF (30 ml) was added sodium hydride (1.58 g, 65.8 mmol). The reaction mixture was stirred at room temperature for 45 minutes followed by dropwise addition of a solution of 1-iodobutane (9.68 g, 52.6 mmol) in anhydrous DMF (10 ml). After the addition, the stirring was continued at room temperature overnight. The reaction mixture was cooled to 0° C. and methanol (5 ml) was added to quench excess sodium hydride. The mixture was partitioned between ethyl acetate (200 ml) and water (150 ml). The organic phase was separated and washed with water (4×100 ml), brine (100 ml) and dried over sodium sulfate. Flash chromatographic purification (25% EtoAc/Hex.) gave n-butyl isourea 2 ( 10.5 g, 92% yd): MS(NH$_3$-CI/DDIP) (M+H$^+$)437.2(100%); $^1$H NMR(300 MHz, CDCl$_3$, 25° C.) δ7.23 (m, 10H), 4.19 (m, 3H), 3.64 (m, 1H), 3.44 (s, 3H), 3.36 (m, 1H), 3.02 (m, 2H), 2.76 (m, 2H), 2.04 (m, 1H), 1.52 (s, 3H), 1.49 (s, 3H), 1.21 (m, 4H), 0.82 (t, J=7.0 Hz, 3H).

PART C: (4R, 5S, 6S, 7R)-Hexahydro-1-[(3-cyano-4-fluorophenyl)methyl]-5,6-O-isopropylidene-4,7-bis-(4-phenylmethyl)-3-phenylmethyl-2H-1,3-diazapin-2-one (3).

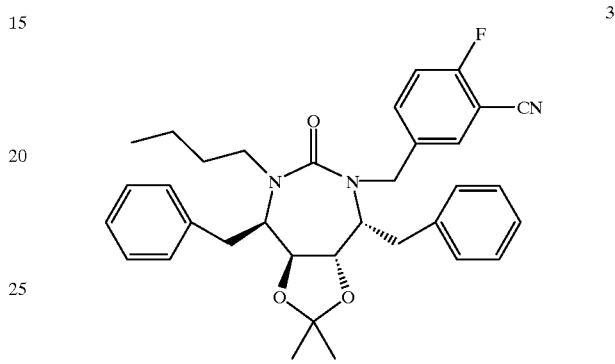

3

To a solution of 2 ( 5.0 g, 11.5 mmol) in acetonitrile (40 ml) was added 4-fluoro-3-cyanobenzyl bromide (3.68 g, 17.25 mmol). The reaction mixture was refluxed overnight. After the solvent was removed under reduced pressure, the residue was purified using flash chromatography ( 35% EtoAc/Hex.) to give cyclic urea 3 as a white solid (4.5 g, 71% yd): MS(NH$_3$-CI/DDIP) (M+H$^+$)556.3(100%); $^1$H NMR(300 MHz, CDCl$_3$, 25° C.) δ7.41 (m, 1H), 7.28 (m, 7H), 7.13 (d, J=9.2 Hz, 2H), 7.05 (t, J=8.8 Hz, 1H), 6.95 (d, J=9.2 Hz, 2H), 4.50 (d, J=14.0 Hz, 1H), 4.07 (m, 2H), 3.70 (m, 3H), 3.44 (t, J=7.7 Hz, 1H), 2.90 (m, 4H), 2.12 (m, 1H), 1.50 (s, 6H), 1.26 (m, 4H), 0.83 (t, J=7.0 Hz, 3H).

PART D: (4R, 5S, 6S, 7R)-Hexahydro-1-[5-(3-aminoindazole)methyl]-3-butyl-5,6-dihydroxy-4,7-bis[phenylmethyl]-2H-1,3-diazapin-2-one (I)

To a solution of 3 ( 4.5 g, 8.11 mmol) in n-butanol (20 ml) was added hydrazine hydrate ( 0.81 g, 16.2 mmol). The mixture was refluxed for 6 hr. The solvent and excess hydrazine were removed under reduced pressure. The residue was dissolved in anhydrous methanol (20 ml) followed by the addition of 4 M HCl in dioxane (2ml). The reaction mixture was stirred at room temperature for 2 hr. Methanol was removed and the residue was partitioned between ethyl acetate (80 ml) and sodium bicarbonate (sat.) (50 ml). The organic phase was separated, washed with water (2×50 ml) and dried over sodium sulfate (anhydrous). Flash chromatographic purification gave I (3.0 g, 72% yd.) as a white solid: MP 129–131° C.; MS(NH$_3$-CI/DDIP) (M+H$^+$) 528.3 (100%); HRMS calcd for C$_{31}$H$_{37}$N$_5$O$_3$+1 528.2975, found 528.2958; $^1$H NMR(300 MHz, CD$_3$OD, 25° C.) δ7.19 (m, 12H), 6.98 (d, J=1.5 Hz, 2H), 4.74 (d, J=13.9 Hz, 1H), 3.85 (dd, J=10.25, 4.76 Hz, 1H), 3.65 (m, 1H), 3.56 (m, 4H), 3.15 (m, 2H), 2.96 (m, 3H), 2.07 (m, 2H), 1.37 (m, 2H), 1.22 (m, 2H), 0.84 (t, J=7.0, 3H).

Utility

The compounds of formula I possess HIV protease inhibitory activity and are therefore useful as antiviral agents for the treatment of HIV infection and associated diseases. The compounds of formula I possess HIV protease inhibitory activity and are effective as inhibitors of HIV growth. The ability of the compounds of the present invention to inhibit viral growth or infectivity is demonstrated in standard assay of viral growth or infectivity, for example, using the assay described below.

The compounds of formula I of the present invention are also useful for the inhibition of HIV in an ex vivo sample containing HIV or expected to be exposed to HIV. Thus, the compounds of the present invention may be used to inhibit HIV present in a body fluid sample (for example, a serum or semen sample) which contains or is suspected to contain or be exposed to HIV.

The compounds provided by this invention are also useful as standard or reference compounds for use in tests or assays for determining the ability of an agent to inhibit viral clone replication and/or HIV protease, for example in a pharmaceutical research program. Thus, the compounds of the present invention may be used as a control or reference compound in such assays and as a quality control standard. The compounds of the present invention may be provided in a commercial kit or container for use as such standard or reference compound.

Since the compounds of the present invention exhibit specificity for HIV protease, the compounds of the present invention may also be useful as diagnostic reagents in diagnostic assays for the detection of HIV protease. Thus, inhibition of the protease activity in an assay (such as the assays described herein) by a compound of the present invention would be indicative of the presence of HIV protease and HIV virus.

As used herein "$\mu g$" denotes microgram, "mg" denotes milligram, "g" denotes gram, "$\mu L$" denotes microliter, "mL" denotes milliliter, "L" denotes liter, "nM" denotes nanomolar, "$\mu M$" denotes micromolar, "mM" denotes millimolar, "M" denotes molar and "nm" denotes nanometer. "Sigma" stands for the Sigma-Aldrich Corp. of St. Louis, Mo.

HIV RNA Assay
DNA Plasmids and in Vitro RNA Transcripts

Plasmid pDAB 72 containing both gag and pol sequences of BH10 (bp 113-1816) cloned into PTZ 19R was prepared according to Erickson-Viitanen et al. *AIDS Research and Human Retroviruses* 1989, 5, 577. The plasmid was linearized with Bam HI prior to the generation of in vitro RNA transcripts using the Riboprobe Gemini system II kit (Promega) with T7 RNA polymerase. Synthesized RNA was purified by treatment with RNase free DNAse (Promega), phenol-chloroform extraction, and ethanol precipitation. RNA transcripts were dissolved in water, and stored at −70° C. The concentration of RNA was determined frow the $A_{260}$.

Probes

Biotinylated capture probes were purified by HPLC after synthesis on an Applied Biosystems (Foster City, Calif.) DNA synthesizer by addition of biotin to the 5' terminal end of the oligonucleotide, using the biotin-phosphoramidite reagent of Cocuzza, *Tet. Lett.* 1989, 30, 6287. The gag biotinylated capture probe (5-biotin-CTAGCTCCCTGCTTGCCCATACTA 3') was complementary to nucleotides 889–912 of HXB2 and the pol biotinylated capture probe (5'-biotin-CCCTATCATTTTTGGTTTCCAT 3') was complementary to nucleotides 2374–2395 of HXB2. Alkaline phosphatase conjugated oligonucleotides used as reporter probes were prepared by Syngene (San Diego, Calif.). The pol reporter probe (5' CTGTCTTACTTTGATAAAACCTC 3') was complementary to nucleotides 2403–2425 of HXB2. The gag reporter probe (5' CCCAGTATTTGTCTACAGCCT-TCT 3') was complementary to nucleotides 950–973 of HXB2. All nucleotide positions are those of the GenBank Genetic Sequence Data Bank as accessed through the Genetics Computer Group Sequence Analysis Software Package (Devereau *Nucleic Acids Research* 1984, 12, 387). The reporter probes were prepared as 0.5 $\mu M$ stocks in 2×SSC (0.3 M NaCl, 0.03 M sodium citrate), 0.05 M Tris pH 8.8, 1 mg/mL BSA. The biotinylated capture probes were prepared as 100 $\mu M$ stocks in water.

Streptavidin Coated Plates

Streptavidin coated plates were obtained from Du Pont Biotechnology Systems (Boston, Mass.).

Cells and Virus Stocks

MT-2 and MT-4 cells were maintained in RPMI 1640 supplemented with 5% fetal calf serum (FCS) for MT-2 cells or 10% FCS for MT-4 cells, 2 mM L-glutamine and 50 $\mu g$/mL gentamycin, all from Gibco. HIV-1 RF was propagated in MT-4 cells in the same medium. Virus stocks were prepared approximately 10 days after acute infection of MT-4 cells and stored as aliquots at −70° C. Infectious titers of HIV-1(RF) stocks were 1–3×10$^7$ PFU (plaque forming units)/mL as measured by plaque assay on MT-2 cells (see below). Each aliquot of virus stock used for infection was thawed only once.

For evaluation of antiviral efficacy, cells to be infected were subcultured one day prior to infection. On the day of infection, cells were resuspended at 5×10$^5$ cells/mL in RPMI 1640, 5% FCS for bulk infections or at 2×10$^6$/mL in Dulbecco's modified Eagles medium with 5% FCS for infection in microtiter plates. Virus was added and culture continued for 3 days at 37° C.

HIV RNA Assay

Cell lysates or purified RNA in 3 M or 5 M GED were mixed with 5 M GED and capture probe to a final guanidinium isothiocyanate concentration of 3 M and a final biotin oligonucleotide concentration of 30 nM. Hybridization was carried out in sealed U bottom 96 well tissue culture plates (Nunc or Costar) for 16–20 hours at 37° C. RNA hybridization reactions were diluted three-fold with deionized water to a final guanidinium isothiocyanate concentration of 1 M and aliquots (150 $\mu L$) were transferred to streptavidin coated microtiter plates wells. Binding of capture probe and capture probe-RNA hybrid to the immobilized streptavidin was allowed to proceed for 2 hours at room temperature, after which the plates were washed 6 times with DuPont ELISA plate wash buffer (phosphate buffered saline(PBS), 0.05% Tween 20.) A second hybridization of reporter probe to the immobilized complex of capture probe and hybridized target RNA was carried out in the washed streptavidin coated well by addition of 120 $\mu l$ of a hybridization cocktail containing 4×SSC, 0.66% Tritonx 100, 6.66% deionized formamide, 1 mg/mL BSA and 5 nM reporter probe. After hybridization for one hour at 37° C., the plate was again washed 6 times. Immobilized alkaline phosphatase activity was detected by addition of 100 $\mu L$ of 0.2 mM 4-methylumbelliferyl phosphate (MUBP, JBL Scientific) in buffer δ(2.5 M diethanolamine pH 8.9 (JBL Scientific), 10 mM MgCl$_2$, 5 mM zinc acetate dihydrate and 5 mM N-hydroxyethyl-ethylene-diamine-triacetic acid). The plates were incubated at 37° C. Fluorescence at 450 nM was measured using a microplate fluorometer (Dynateck) exciting at 365 nM.

Microplate Based Compound Evaluation in HIV-1 Infected MT-2 Cells

Compounds to be evaluated were dissolved in DMSO and diluted in culture medium to twice the highest concentration to be tested and a maximum DMSO concentration of 2%. Further three-fold serial dilutions of the compound in culture medium were performed directly in U bottom microtiter plates (Nunc). After compound dilution, MT-2 cells (50 µL) were added to a final concentration of $5 \times 10^5$ per mL ($1 \times 10^5$ per well). Cells were incubated with compounds for 30 minutes at 37° C. in a $CO_2$ incubator. For evaluation of antiviral potency, an appropriate dilution of HIV-1 (RF) virus stock (50 µL) was added to culture wells containing cells and dilutions of the test compounds. The final volume in each well was 200 µL. Eight wells per plate were left uninfected with 50 µL of medium added in place of virus, while eight wells were infected in the absence of any antiviral compound. For evaluation of compound toxicity, parallel plates were cultured without virus infection.

After 3 days of culture at 37° C. in a humidified chamber inside a $CO_2$ incubator, all but 25 µL of medium/well was removed from the HIV infected plates. Thirty seven µL of 5 M GED containing biotinylated capture probe was added to the settled cells and remaining medium in each well to a final concentration of 3 M GED and 30 nM capture probe. Hybridization of the capture probe to HIV RNA in the cell lysate was carried out in the same microplate well used for virus culture by sealing the plate with a plate sealer (Costar), and incubating for 16–20 hrs in a 37° C. incubator. Distilled water was then added to each well to dilute the hybridization reaction three-fold and 150 µL of this diluted mixture was transferred to a streptavidin coated microtiter plate. HIV RNA was quantitated as described above. A standard curve, prepared by adding known amounts of pDAB 72 in vitro RNA transcript to wells containing lysed uninfected cells, was run on each microtiter plate in order to determine the amount of viral RNA made during the infection.

In order to standardize the virus inoculum used in the evaluation of compounds for antiviral activity, dilutions of virus were selected which resulted in an $IC_{90}$ value (concentration of compound required to reduce the HIV RNA level by 90%) for dideoxycytidine (ddC) of 0.2 µg/mL. $IC_{90}$ values of other antiviral compounds, both more and less potent than ddC, were reproducible using several stocks of HIV-1 (RF) when this procedure was followed. This concentration of virus corresponded to $\sim 3 \times 10^5$ PFU (measured by plaque assay on MT-2 cells) per assay well and typically produced approximately 75% of the maximum viral RNA level achievable at any virus inoculum. For the HIV RNA assay, $IC_{90}$ values were determined from the percent reduction of net signal (signal from infected cell samples minus signal from uninfected cell samples) in the RNA assay relative to the net signal from infected, untreated cells on the same culture plate (average of eight wells). Valid performance of individual infection and RNA assay tests was judged according to three criteria. It was required that the virus infection should result in an RNA assay signal equal to or greater than the signal generated from 2 ng of pDAB 72 in vitro RNA transcript. The $IC_{90}$ for ddC, determined in each assay run, should be between 0.1 and 0.3 µg/mL. Finally, the plateau level of viral RNA produced by an effective protease inhibitor should be less than 10% of the level achieved in an uninhibited infection. A compound was considered active if its $IC_{90}$ was found to be less than 1 µM.

For antiviral potency tests, all manipulations in microtiter plates, following the initial addition of 2× concentrated compound solution to a single row of wells, were performed using a Perkin Elmer/Cetus ProPette.

Dosage and Formulation

The antiviral compounds of this invention can be administered as treatment for viral infections by any means that produces contact of the active agent with the agent's site of action, i.e., the viral protease, in the body of a mammal. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences,* supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 ml contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

Combination of components (a) and (b)

Each therapeutic agent component of this invention can independently be in any dosage form, such as those described above, and can also be administered in various ways, as described above. In the following description component (b) is to be understood to represent one or more agents as described previously. Thus, if components (a) and (b) are to be treated the same or independently, each agent of component (b) may also be treated the same or independently.

Components (a) and (b) of the present invention may be formulated together, in a single dosage unit (that is, combined together in one capsule, tablet, powder, liquid, etc.) as a combination product. When component (a) and (b) are not formulated together in a single dosage unit, component (a) may be administered at the same time as component (b) or in any order; for example component (a) of this invention may be administered first, followed by administration of component (b), or they may be administered in the reverse order. If component (b) contains more that one agent, e.g., one RT inhibitor and one protease inhibitor, these agents may be administered together or in any order. When not administered at the same time, preferably the administration of component (a) and (b) occurs less than about one hour apart. Preferably, the route of administration of component (a) and (b) is oral. The terms oral agent, oral inhibitor, oral compound, or the like, as used herein, denote compounds which may be orally administered. Although it is preferable that component (a) and component (b) both be administered by the same route (that is, for example, both orally) or dosage form, if desired, they may each be administered by different routes (that is, for example, one component of the combination product may be administered orally, and another component may be administered intravenously) or dosage forms.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (a) and (b) of the present invention will be readily ascertainable by a medical practitioner skilled in the art, based upon the present disclosure. By way of general guidance, typically a daily dosage may be about 100 milligrams to about 1.5 grams of each component. If component (b) represents more than one compound, then typically a daily dosage may be about 100 milligrams to about 1.5 grams of each agent of component (b). By way of general guidance, when the compounds of component (a) and component (b) are administered in combination, the dosage amount of each component may be reduced by about 70–80% relative to the usual dosage of the component when it is administered alone as a single agent for the treatment of HIV infection.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines.

Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose or other appropriate materials as known in the art, in order to further separate the active components. The polymer coating serves to form an additional barrier to interaction with the other component. In each formulation wherein contact is prevented between components (a) and (b) via a coating or some other material, contact may also be prevented between the individual agents of component (b).

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of HIV infection, which comprise a therapeutically effective amount of a pharmaceutical composition comprising a compound of component (a) and one or more compounds of component (b), in one or more sterile containers, are also within the ambit of the present invention. Sterilization of the container may be carried out using conventional sterilization methodology well known to those skilled in the art. Component (a) and component (b) may be in the same sterile container or in separate sterile containers. The sterile containers of materials may comprise separate containers, or one or more multi-part containers, as desired. Component (a) and component (b), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter Patent of United States is:

1. A pharmaceutical composition, comprising: a pharmaceutically acceptable carrier and a therapeutically effective amount of a compound of formula I:

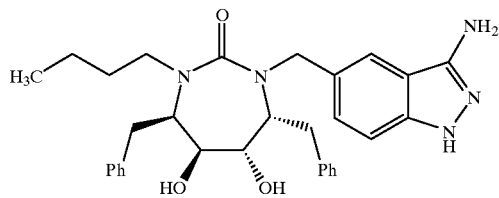

or a pharmaceutically acceptable salt form thereof or a compound wherein the two hydroxy groups of formula I join to form a moiety selected from the group: epoxide —OCH₂SCH₂O—, —OC(=O)O—, —OCH₂O—, —OC(=S)O—, —OC(=O)C(=O)O—, —OC(CH₃)₂O—, —OC((CH₂)₃NH₂)(CH₃)O—, —OC(OCH₃)CH₂(CH₂CH₃)O—, and —OS(=O)O— or a pharmaceutically acceptable salt form thereof.

2. A pharmaceutical composition of claim 1, further comprising: at least one compound selected from the group consisting of HIV reverse transcriptase inhibitors and HIV protease inhibitors.

3. A composition of claim 1, wherein the compound is of formula I or a pharmaceutically acceptable salt form thereof.

4. A composition of claim 3, wherein the pharmaceutically acceptable salt of formula I is selected from: hydrochloric acid salt, hydrobromic acid salt, sulfuric acid salt, phosphoric acid salt, acetic acid salt, succinic acid salt, glycolic acid salt, stearic acid salt, lactic acid salt, malic acid salt, tartaric acid salt, citric acid salt, ascorbic acid salt, maleic acid salt, fumaric acid salt, toluenesulfonic acid salt, methanesulfonic acid salt, and oxalic acid salt.

5. A pharmaceutical composition of claim 3, further comprising: at least one compound selected from the group consisting of HIV reverse transcriptase inhibitors and HIV protease inhibitors.

6. A method for treating HIV infection which comprises administering to a host in need of such treatment a therapeutically effective amount of a compound of formula I:

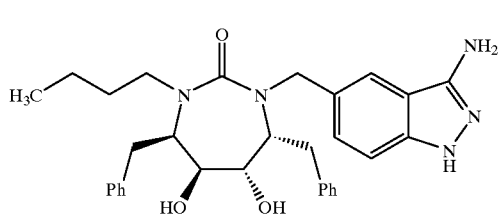

or a pharmaceutically acceptable salt form thereof or a compound wherein the two hydroxy groups of formula I join to form a moiety selected from the group: epoxide —OCH₂SCH₂O—, —OC(=O)O—, —OCH₂O—, —OC(=S)O—, —OC(=O)C(=O)O—, —OC(CH₃)₂O—, —OC((CH₂)₃NH₂)(CH₃)O—, —OC(OCH₃)(CH₂CH₂CH₃)O—, and —OS(=O)O— or a pharmaceutically acceptable salt form thereof.

7. A method of claim 6, further comprising administering, in combination with the compound of formula I, at least one compound selected from the group consisting of HIV reverse transcriptase inhibitors and HIV protease inhibitors.

8. A method of claim 6, wherein the compound is of formula I or a pharmaceutically acceptable salt form thereof.

9. A method of claim 8, wherein the pharmaceutically acceptable salt of formula I is selected from: hydrochloric acid salt, hydrobromic acid salt, sulfuric acid salt, phosphoric acid salt, acetic acid salt, succinic acid salt, glycolic acid salt, stearic acid salt, lactic acid salt, malic acid salt, tartaric acid salt, citric acid salt, ascorbic acid salt, maleic acid salt, fumaric acid salt, toluenesulfonic acid salt, methanesulfonic acid salt, and oxalic acid salt.

10. A method of claim 8, further comprising administering, in combination with the compound of formula I, at least one compound selected from the group consisting of HIV reverse transcriptase inhibitors and HIV protease inhibitors.

11. A method of claim 10, wherein the reverse transcriptase inhibitor is a nucleoside reverse transcriptase inhibitor.

12. A method of claim 11, wherein the nucleoside reverse transcriptase inhibitor is selected from AZT, 3TC, ddI, ddC, and d4T and the protease inhibitor is selected from saquinavir, ritonavir, indinavir, VX-478, nelfinavir, KNI-272, CGP-61755, and U-103017.

13. A method of claim 12, wherein the nucleoside reverse transcriptase inhibitor is selected from AZT and 3TC and the protease inhibitor is selected from saquinavir, ritonavir, and indinavir.

14. A method of claim 13, wherein the nucleoside reverse transcriptase inhibitor is AZT.

15. A method of claim 13, wherein the protease inhibitor is indinavir.

16. A method of claim 13, wherein the pharmaceutically acceptable salt of formula I is selected from: hydrochloric acid salt, hydrobromic acid salt, sulfuric acid salt, phosphoric acid salt, acetic acid salt, succinic acid salt, glycolic acid salt, stearic acid salt, lactic acid salt, malic acid salt, tartaric acid salt, citric acid salt, ascorbic acid salt, maleic acid salt, fumaric acid salt, toluenesulfonic acid salt, methanesulfonic acid salt, and oxalic acid salt.